US008175691B2

(12) United States Patent  
Huldt

(10) Patent No.: US 8,175,691 B2  
(45) Date of Patent: May 8, 2012

(54) ECG ELECTRODE AND ELECTRODE SUPPORT

(75) Inventor: Olof Huldt, Malmö (SE)

(73) Assignee: Physio-Control, Inc., Redmond, WA (US)

( * ) Notice: Subject to any disclaimer, the term of this patent is extended or adjusted under 35 U.S.C. 154(b) by 425 days.

(21) Appl. No.: 12/304,575

(22) PCT Filed: Jun. 11, 2007

(86) PCT No.: PCT/SE2007/000559
§ 371 (c)(1),
(2), (4) Date: Aug. 19, 2009

(87) PCT Pub. No.: WO2007/145562
PCT Pub. Date: Dec. 21, 2007

(65) Prior Publication Data
US 2009/0326400 A1 Dec. 31, 2009

(30) Foreign Application Priority Data

Jun. 14, 2006 (SE) ........................................ 0601300

(51) Int. Cl.
*A61B 5/04* (2006.01)
(52) U.S. Cl. ........................................................ 600/509
(58) Field of Classification Search ................ 600/509
See application file for complete search history.

(56) References Cited

U.S. PATENT DOCUMENTS

| 3,476,104 | A |   | 11/1969 | Davis |
| 3,888,240 | A |   | 6/1975 | Reinhold, Jr. et al. |
| 3,954,100 | A | * | 5/1976 | Sem-Jacobsen ............... 600/393 |
| 4,082,086 | A |   | 4/1978 | Page et al. |
| 5,509,822 | A |   | 4/1996 | Negus et al. |
| 6,179,793 | B1 | * | 1/2001 | Rothman et al. ................. 601/44 |
| 2004/0230140 | A1 |   | 11/2004 | Steen |

FOREIGN PATENT DOCUMENTS

| EP | 0 459 239 A2 | 12/1991 |
| WO | WO 2004/112683 | 12/2004 |

OTHER PUBLICATIONS

International Search Report dated Jul. 12, 2007, issued in international application no. PCT/SE2007/000559.
Marsden, J E: "Cardiac Rhythmicity". Mathematical Physiology, New York, Springer-Verlag, 1998, ISBN 0-387-98381-3, pp. 379-388, especially p. 386, line 3-line 13.
Engblom H et al: "The relationship between electrical axis by 12-lead electrocardiogram and anatomical axis of the heart by cardiac magnetic resonance in healthy subjects". Am. Heart J. 2005, vol. 150, p. 507-p. 512.

* cited by examiner

Primary Examiner — George Manuel
(74) Attorney, Agent, or Firm — Marger Johnson & McCollom PC

(57) ABSTRACT

An electrically non-conductive back plate for supporting the back of a patient in a supine position comprises on its front face facing the back of the patient a pair or more of ECG electrodes capable of maintaining electrically conductive skin contact with the patient's back. The pair of ECG electrodes is disposed at a sharp angle with the mean heart vector, in particular so as to form an angle β of about 45°±25° with the projection S of the patient's spine on the back plate. Also disclosed is an ECG electrode for mounting in a recess of the back plate and an apparatus for treating cardiac arrest by compression of the sternum comprising the back plate.

13 Claims, 6 Drawing Sheets

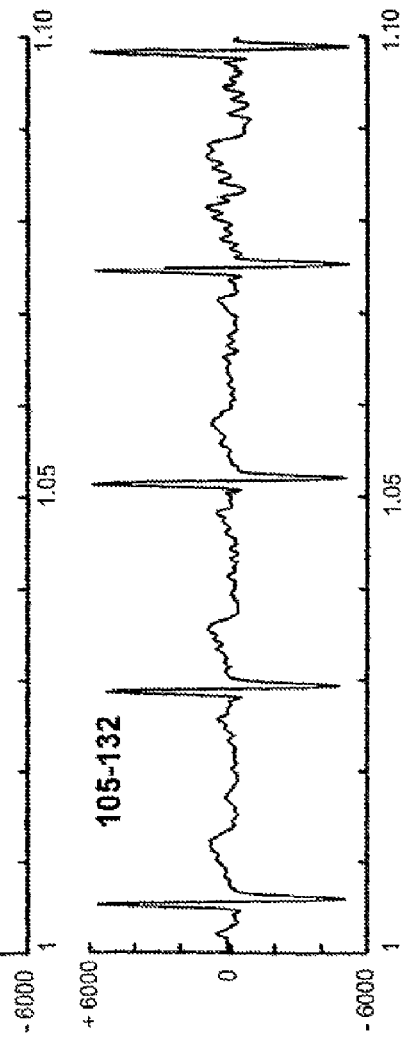
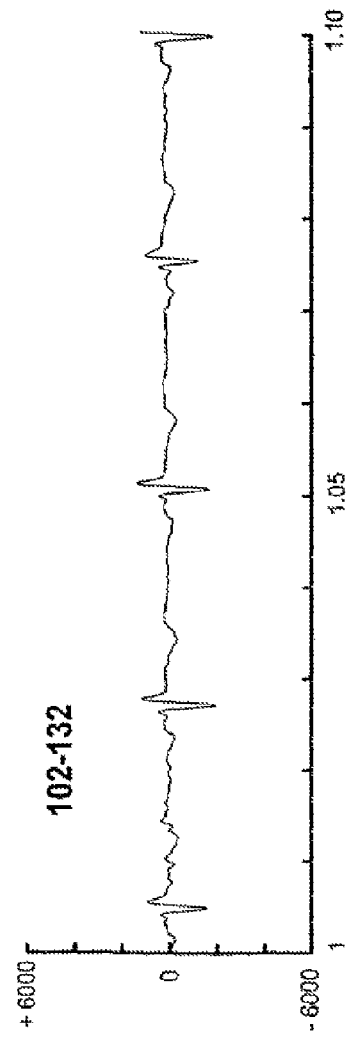
FIG. 6A
FIG. 6B
FIG. 6C

ECG ELECTRODE AND ELECTRODE SUPPORT

CROSS REFERENCE TO RELATED APPLICATIONS

The present application is a 35 U.S.C. §371 National Phase conversion of PCT/SE2007/000559, filed Jun. 11, 2007, which claims benefit of Swedish Application No. 0601300-7, filed Jun. 14, 2006, the disclosure of which is incorporated herein by reference. The PCT International Application was published in the English language.

FIELD OF THE INVENTION

The present invention relates to an ECG electrode and a support on which the ECG electrode is mounted, in particular for use in apparatus for treating sudden cardiac arrest.

BACKGROUND OF THE INVENTION

Sudden cardiac arrest is commonly treated mechanically and/or by electrical defibrillation. Mechanical treatment may be given manually or by a chest compression apparatus. A number of chest compression apparatus are known in the art, such as the pneumatically driven LUCAS™ mechanical chest compression system ("Lucas™ system"; an apparatus for compression and physiological in Cardio-Pulmonary Resuscitation, CPR, manufactured by Jolife A B, Lund, Sweden). Specifically the Lucas™ system comprises a support structure and a compression unit. The support structure includes a back plate for positioning the patient's back posterior to the patient's heart and a front part for positioning around the patient's chest anterior to the heart. The front part has two legs, each having a first end pivotally connected to at least one hinge of the front part and a second end removably attachable to the back plate. The front part is devised to centrally receive the compression unit which is arranged to repeatedly compress the patient's chest when the front part is attached to the back plate. The compression unit comprises a pneumatic unit arranged to drive and control compression, an adjustable suspension unit to which a compression pad is attached, and a means for controlling the position of the pad in respect of the patient's chest. Defibrillation may be provided independently of and concomitant.

In deciding when and for how long time to administer compressions to the patient it is important to measure the electrical activity of the heart. This is accomplished by using a movable ECG apparatus separate of the mechanical compression system.

ECG apparatus of this kind comprise a number of ECG electrodes connected to the apparatus by flexible conductors. Before the start of measurement the ECG electrodes have to be attached to the chest of the patient in a given pattern. In a situation of urgency such as one of cardiac arrest this is time consuming and should be avoided.

EP 459 239 A2 discloses a portable device for sensing cardiac function and automatically delivering electrical therapy comprising torsion spring operated electrode assemblies.

WO 2004/112683 A1 discloses an electrical means for providing electrostimulation comprising two electrodes, a front electrode to be applied on the chest of the patient adjacent to the pad, plate or disc, etc. of the reciprocating means or integrated in the pad, plate or disc, etc., and a rear electrode to be applied to the back of the patient integrated into the back plate so as to be disposed about perpendicularly under the sternum if the patient is resting in a correct position on the back plate. The electrodes of the means for providing electrostimulation may be additionally used for picking up ECG signals and forwarding them to an ECG registration and analysis unit. The ECG signals obtainable in this manner are however strongly affected by the movement of sternum during compression, which impairs their quality. The present invention seeks to remedy this problem.

OBJECTS OF THE INVENTION

It is an object of the present invention to provide an ECG electrode for use in apparatus for treating sudden cardiac arrest in a patient by compression of the sternum, which is easily attached to the skin of the patient's back.

It is a another object of the invention to provide an ECG electrode for use in apparatus for treating sudden cardiac arrest by compression of the sternum, which is not or only moderately affected by the movement of sternum.

It is a further object of the invention to provide a support, in particular a back plate, comprising one or more ECG electrodes in a given pattern.

Still further objects of the invention will be evident from the following summary of the invention, the description of preferred embodiments thereof illustrated in a drawing, and the appended claims.

SUMMARY OF THE INVENTION

According to the present invention is disclosed a support for supporting the back of a patient in a supine position comprising a pair or more of ECG electrodes capable of maintaining electrically conductive skin contact with the patient's back. The support is electrically non-conductive, generally flat and adapted to the portion of the back which it is intended to receive for support. It may have, for instance, about rectangular or other symmetric oblong form, in which case the long side of the rectangle or similar extends about perpendicular to a projection the patient's spine on the support. The support is preferably of a kind allowing the patient to be centered on the support in a supine position. In the following the support of the invention will be termed "back plate"; the face of the back plate facing the back of the patient will be termed "front face".

According to a first preferred aspect of the invention the back plate is comprised by an apparatus for treating cardiac arrest by compression of the sternum.

According to a second preferred aspect of the invention the line connecting the at least one pair of the one or more pairs of ECG electrodes is disposed at an angle $\alpha$ of $5°\pm25°$, more preferred of $5°\pm15°$, with the perpendicular projection on the back plate of the long heart axis of a person of whom the chest is supported by the back plate; the angle $\alpha$ is the one defined by the line/projection in a caudal direction from their point of intersection. In this application "long heart axis" denotes the direction of a line connecting the center of the mitral annulus and the left ventricular apex at the end of the diastolic phase. The direction of the long heart axis in a frontal plane is about $40°\pm20°$ (H Engblom et al, Am Heart J 2005, 150(3); 507-512). According to the invention it is thus preferred for a line connecting said at least one pair of the one pair or more of ECG electrodes to be comprised by an angle $\beta$ of about $45°\pm25°$, more preferred of about $45°\pm15°$, formed with the projection S of the spine of a person of which the chest is supported by the back plate. In a generally symmetric back plate the projection S may be equalled with an imagined short mirror line disposed on the front face of the back plate. The angle β is the one defined by the line connecting the pair of electrodes and the projection S in a caudal direction from their point of intersection.

According to the present invention is also disclosed an apparatus for treating cardiac arrest by compression of the sternum, comprising the aforementioned back plate of the invention provided with one pair or more of the ECG electrodes. It is preferred for the back plate to be easily mountable on/detachable from the main portion of the apparatus for treating cardiac arrest.

According to a third preferred aspect of the invention is disclosed an ECG electrode capable of being mounted on the back plate so as to face the patient's back and maintaining electrically conductive skin contact. It is preferred for the ECG electrode to be mounted on the back plate in a manner to make it adapt to slight movements of the patient in respect of the back plate without loosing contact; such movements comprise horizontal movements but, in particular, perpendicular and skew movements with an important perpendicular component caused, for instance, by the patient's sternum being repeatedly compressed to establish or maintain circulation. It is thus preferred for the ECG electrode to be displaceable in a horizontal (lateral) direction and/or a vertical direction in respect to the back plate. It is however also possible to use electrodes with the back plate that are rigidly mounted in the back plate and thus are not laterally displaceable in respect of it, for instance needle electrodes such as the electrode disclosed in U.S. Pat. No. 5,509,822, the adaptation for mounting in the back plate is within the easy reach of a person skilled in the art.

According to a fourth preferred aspect the ECG electrode of the invention is mounted displaceable in a horizontal and/or vertical direction in a recess provided in the front face of the back plate.

According to a fifth preferred aspect of the invention the ECG electrode comprises an electrically conductive electrode disk, a resiliently compressible spring means disposed between the electrode disk and the support, and a flexible conducting means for connecting the electrode disk to an ECG monitoring unit. This arrangement minimizes disturbances of the ECG signal by body geometry changes caused by the compression of the sternum. The electrode of the invention is freely movable in the recess in a direction perpendicular to the support while its lateral movement is rather restricted. By the force of a spring means the front face of the electrode is pressed against the skin of the patient's back to provide good electrical contact. Its front face may be provided with electrical contact enhancing means, such as with an electrically conducting gel or paste known in the art.

It is preferred for the electrode disk to be supported by an electrically non-conductive support element, preferably of a rigid polymer material, disposed between the electrode disk and the spring element. Preferably the support element is integral with the electrode disk. The compressible spring means may be a coil, a disc of a resilient foam such as polyurethane foam, a hollow rubber ring or similar. The electrode disk, the support element and/or their combination preferably comprise a cylindrical portion or are substantially cylindrical.

The recess for mounting of the electrode of the invention on the support is disposed on an essentially flat face thereof and has a form preferably allowing the electrode to be fully inserted into the recess against the resilient force of the spring means which, with their one end, abut the bottom of the recess. It is preferred that, in a non-load bearing state, the electrode disk extends from the recess for a short distance. It is preferred for the circumference of the recess and of the electrode disk, the support element, and the combination of electrode disk and support element to be of similar form and diameter similar so as to provide guidance by the side walls of the recess for the movement of the electrode with little play.

According to a sixth preferred aspect of the invention is disclosed an ECG electrode for mounting on a support, in particular the back plate of the invention, capable of lateral displacement in regard of the support.

The invention will now be explained in more detail by reference to preferred embodiments illustrated by a rough drawing.

DESCRIPTION OF THE FIGURES

In the attached drawing is shown in:

FIG. 6a an electrocardiogram obtained by recording the ECG signal of the first electrode pair of FIG. 4;

FIG. 6b an electrocardiogram obtained by recording the ECG signal of the second electrode pair of FIG. 4;

FIG. 6c an electrocardiogram obtained by recording the ECG signal of the third electrode pair of FIG. 4.

DESCRIPTION OF PREFERRED EMBODIMENTS

Figure 1A:
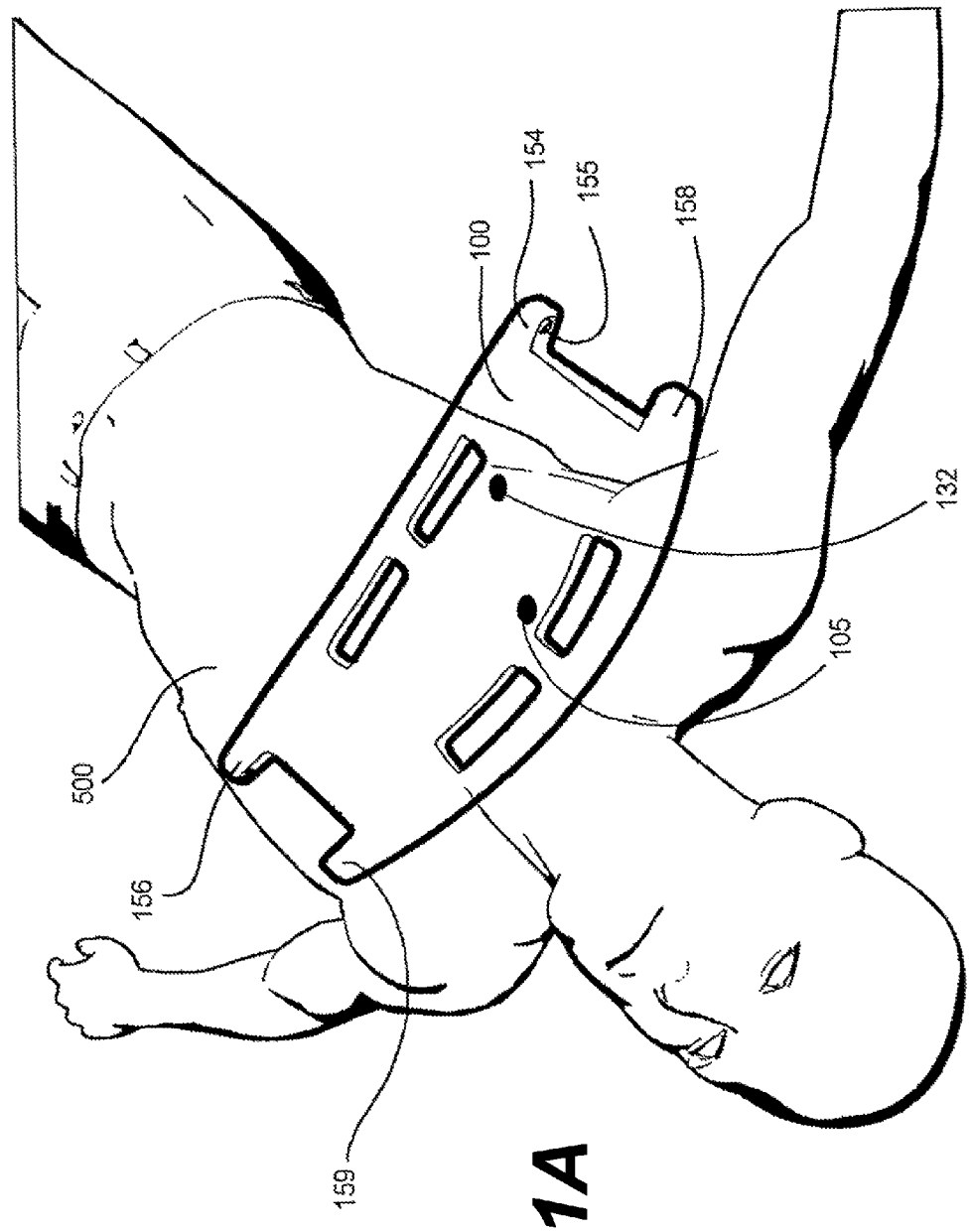
FIG. 1a a patient resting with his transparently shown trunk in a supine position on a back plate pertaining to an apparatus for treating cardiac arrest by compression of the sternum, in a perspective view.
Figure 1B:
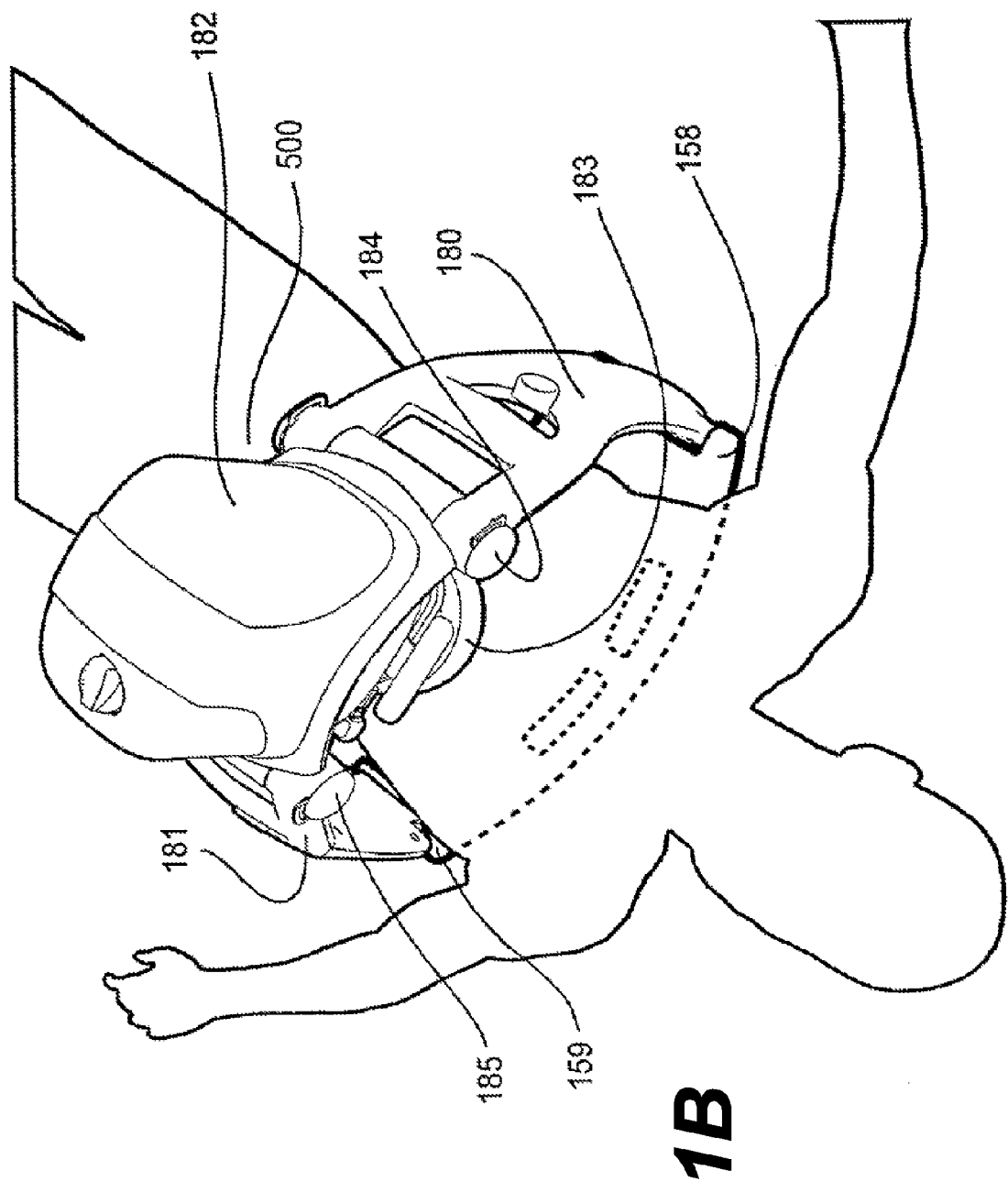
FIG. 1b the patient and the back plate of FIG. 1a, with the remainder of the apparatus mounted to the back plate, in the same view.

FIG. 1a shows a seemingly lifeless patient in a supine position, the trunk 500 of whom has been placed on a back plate 100 resting on a floor. All clothing on the trunk has been removed in preparation for resuscitation by a central unit 182 (FIG. 1b) for compression of the sternum. In FIG. 1b the remainder of the apparatus is shown in a state mounted to the back plate 100. Mounting is accomplished in the following manner: the free ends of curved right 180 and left 181 legs swivelingly attached by means of joints 184 and 185, respectively, to the central pneumatic compression unit 182 from which a reciprocating plunger ending in a suction cup 183 extends towards the sternum of the patient are mounted in lateral brackets 154; 158 and 156; 159 of the back plate 100 provided with bores 155 for releasable insertion of short shafts (not shown) extending from said free ends. Left" and "right" designate positions from the patient's perspective. The apparatus, which shares the general design of the Lucas™ system, encloses the patient in the sternum region. By a reciprocating movement of the plunger and the suction cup 183 the patient's chest is compressed periodically. In its top or apical position the cup 183 abuts the uncompressed chest at the sternum, from which position the compression cycle starts. The compressor unit is driven by compressed air in a gas flask (not shown).

Figure 2:
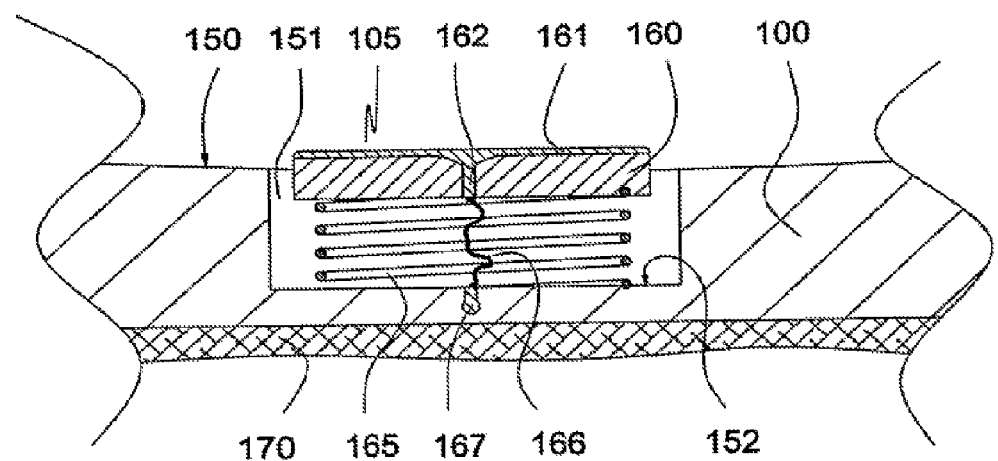
FIG. 2 an ECG electrode of the invention, mounted on a support, in a unrestrained condition and in a sectional view.

On its side facing the patient's back the back plate is provided with two ECG electrodes 105 and 132. One of them, electrode 105, is shown in greater detail in FIGS. 2 and 3.

Figure 3:
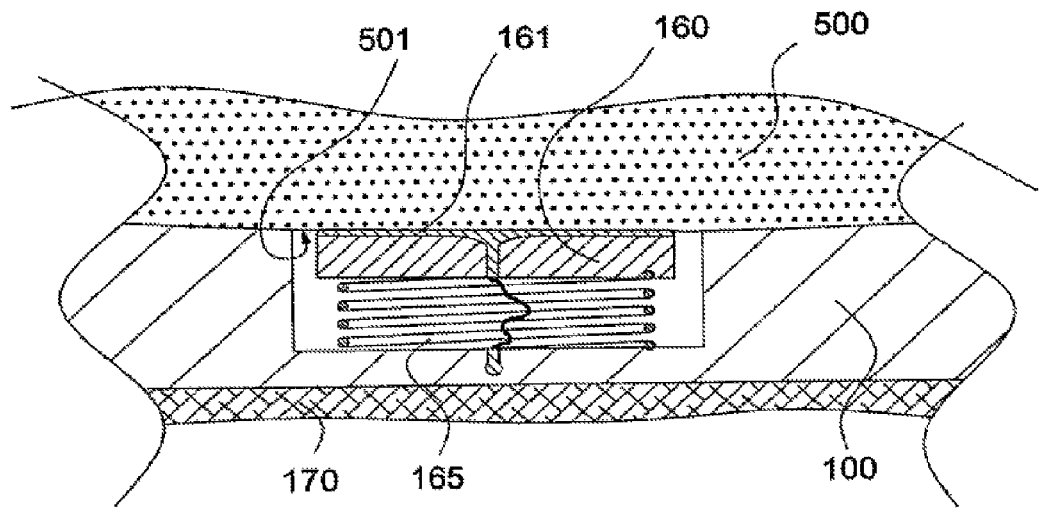
FIG. 3 the ECG electrode of FIG. 2, in the same view but in a restrained condition with the back of a patient resting un the support.

The cylindrical electrode 105 comprises an electrically conductive electrode disk 161 adhesively attached to a nonconductive support element 160 of a suitable polymer like polypropene or polycarbonate, which surrounds a central stem 162 extending from and integral with the electrode disk 161. The electrode disk/support element 161; 160 is mounted in a cylindrical recess 151 in the front face 150 the back plate 100, which rests on a floor 170. The diameter of the recess 151 is slightly larger than the diameter of electrode disk/support element 161; 160 to allow the displacement of the latter combination in a direction perpendicular to the front face 150. A spring coil 165 is firmly attached to the rear side of the support element 160 with its one end and to the bottom 152 of the recess 151 at its other. In its unloaded state shown in FIG. 2 the electrode 105 extends somewhat above the front face 150 of the back plate 100. In its state loaded by the trunk 500 of the patient the front face of the electrode disk 161 is in electrically conducting contact with the patient's skin 501 and level with the front face 150 of the back plate 100. The front face of the electrode disk 161 may even be pressed slightly into the recess 151 by the weight of the trunk and the flexible nature of its soft tissues. This loaded state of the electrode 102 is shown in FIG. 3. Electrical connection of the ECG electrode 102 with an ECG unit (not shown) is provided by means of a flexible electrical conductor 166 attached to the electrode stem 162 at its one end, and to a copper wire 167 moulded into the back plate 100 at its other end. The copper wire 167 is coupled to a contact manifold 169 (FIG. 4) to which also the corresponding copper wire 168 of the other electrode 132 and further electrodes, if any, are coupled. Via the manifold 169 the electrodes 105, 132 can be connected with an ECG monitoring unit, which can be integrated into, for instance, the central pneumatic unit 182 for compression of the sternum, or with a separate hand-held ECG monitoring unit or similar. Connection can be physical or wireless.

Figure 4:
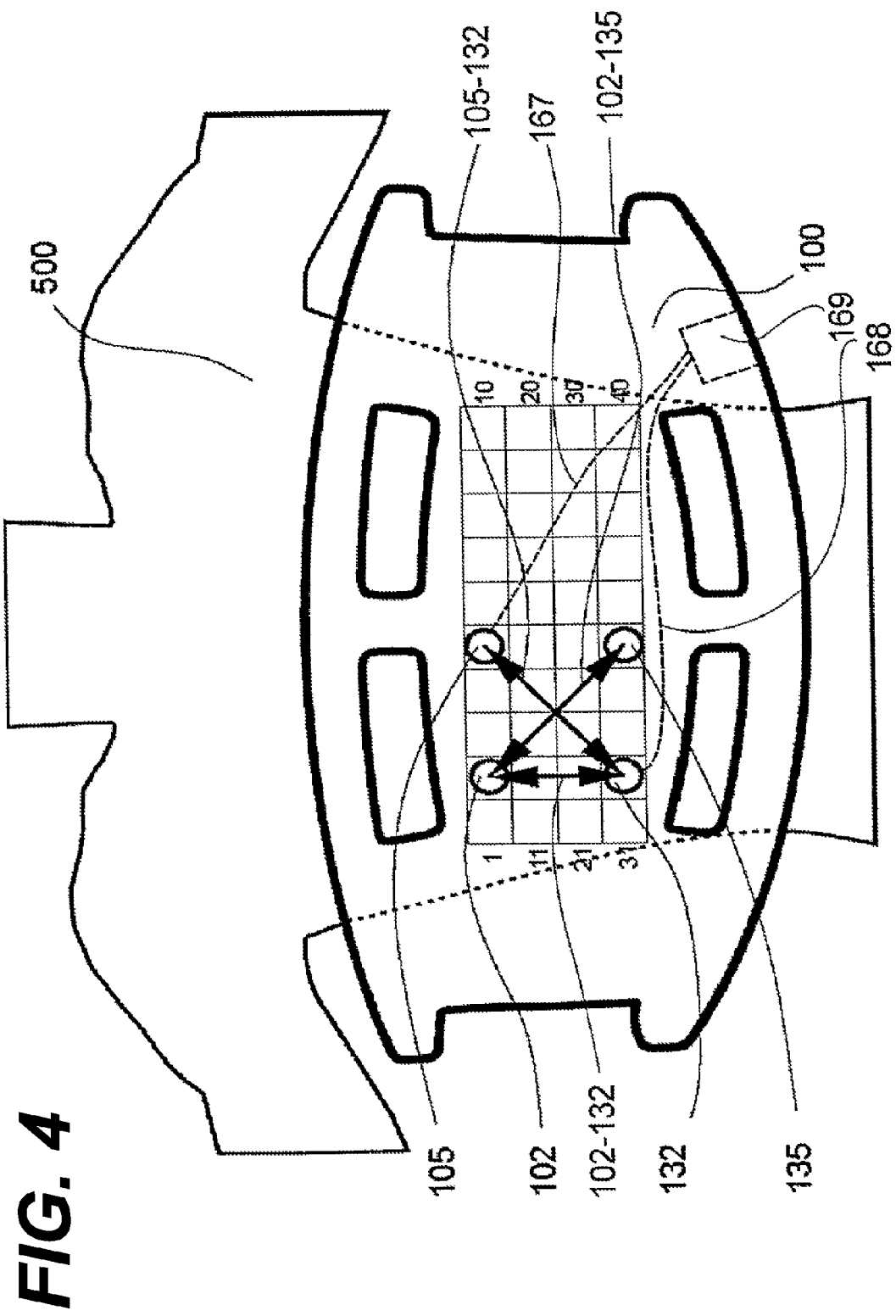
FIG. 4 the back plate of FIGS. 1-3, with the trunk of the patient shown transparent and provided with a first and a second pair of ECG electrodes and their disposition in regard of a positioning grid, in a top view.

FIG. 4 illustrates an area for dorsal electrode placement on the front face of the back plate 100. For easy identification of possible electrode positions the area is defined by a grid of squares comprising ten columns in four rows. The squares are consecutively numbered 1-40 starting at the left upper corner and ending at the right lower corner.

The importance of correct positioning of the electrode pairs is illustrated in FIGS. 6a-6c. While the ECG trace obtained by the electrode pair 102-135 (FIG. 4) disposed on the back of a healthy person in squares 2 and 35, respectively, of the positioning grid of FIG. 4 does not contain useful information, the trace obtained by the electrode pair 105-132 disposed in squares 5 and 32 of the positioning grid (FIG. 4) reflects the sinus rhythm of a normal heartbeat. The ECG trace of the electrode pair 2/32 occupying the intermediate position 102-132 (FIG. 6c) has a form between the extremes 105-132 and 102-135. An ECG signal obtained by electrode pair 105-132 (FIG. 6b) thus can be used to monitor the heartbeat of a patient being administered compressions of the sternum by the apparatus of FIG. 2.

Figure 5:
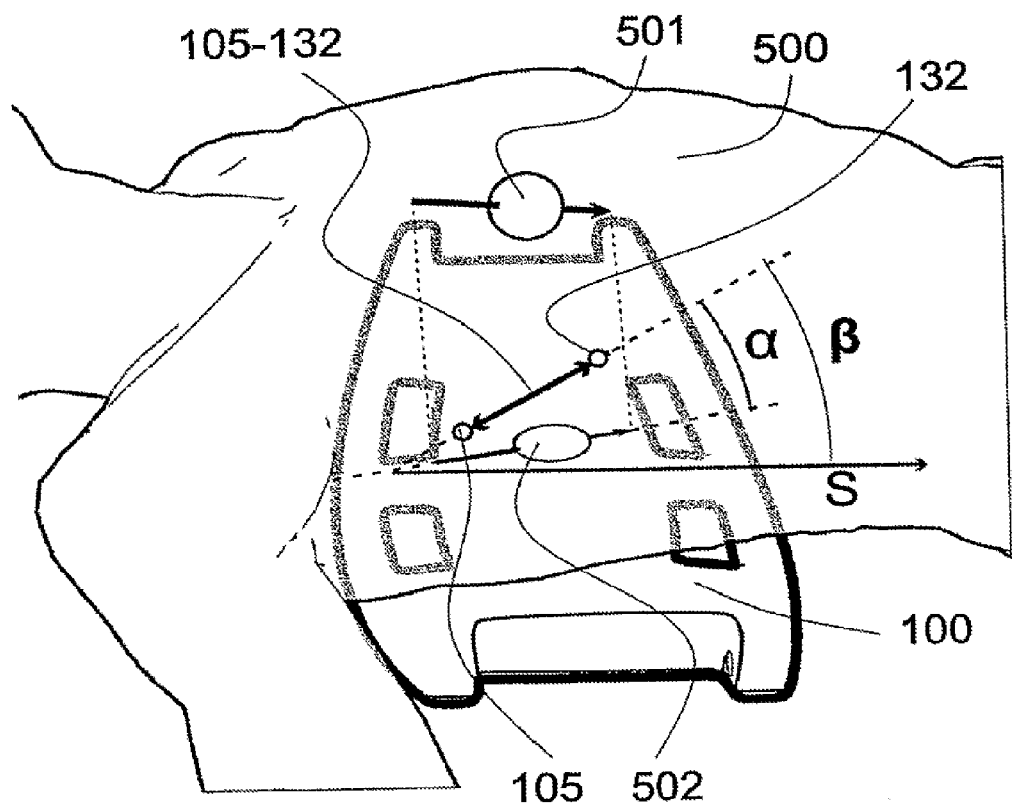
FIG. 5 the chest portion of the patient resting on the back plate, with the first electrode pair of FIG. 4 and electric heart vector shown projected on the back plate, in an oblique lateral view.

Useful ECG electrode pair positions on a back plate are comprised by an angle β of about 45°±25°, preferably of about 45°±15°, formed by the line connecting them with the projection S of the spine on the back plate 100 (FIG. 5) or by an angle α of about 40°±25°, preferably of about 40°±15°, by the line connecting them with the projection 502 on the back plate 100 of the long heart axis 501; in this assessment it is understood that the position of the heart and thus the direction of the long heart axis 501 varies between individuals. The angles α and β are measured in a caudal direction from the point of intersection of the respective lines.

What is claimed is:

1. A back plate for supporting the back of a patient in a supine position, the back plate for use in a system for treating cardiac arrest in a patient, the system including an apparatus for compressing the patient's sternum against the back plate when the patient is in the supine position, the back plate comprising:
    two or more ECG electrodes for maintaining contact with the patient's back when the patient is in the supine position;
    a front face facing the back of the patient when the patient is in the supine position; and one or more recesses in the front face structured to be capable to receive therein at least a first one of the ECG electrodes at one of at least two alternative locations, for obtaining respectively alternative ECG traces of the patient between a second one of the ECG electrodes and the first ECG electrode in the two alternative locations.

2. The back plate of claim 1, in which
the first one of the recesses is structured such that the first ECG electrode is displaceable within the first recess along a direction.

3. The back plate of claim 1, in which
the back plate has two recesses, each capable of receiving therein the first ECG electrode.

4. The back plate of claim 1, in which
the back plate has a plurality of recesses, a number of the recesses being adjacent each other.

5. The back plate of claim 1, in which
the back plate has a plurality of recesses, a number of the recesses being adjacent each other along a direction.

6. The back plate of claim 1, in which
the back plate has a plurality of recesses, a number of the recesses being adjacent each other along two directions.

7. The back plate of claim 1, further comprising:
a spring located wholly within a first one the recesses for biasing the first ECG electrode towards the patient.

8. The back plate of claim 7, in which
the first ECG electrode can be compressed to be fully within the first recess against the resilient force of the spring.

9. The back plate of claim 7, in which
when in a non-load bearing state, the first electrode extends from the first recess by a short distance.

10. The back plate of claim 1, further comprising:
a manifold electrically connected with the first ECG electrode, and
in which the manifold is connected to an ECG monitoring unit.

11. The back plate of claim 10, in which
the manifold is connected with the ECG monitoring unit wirelessly.

12. The back plate of claim 10, in which
the manifold has a physical connection with the ECG monitoring unit.

13. The back plate of claim 10, in which
the system for treating cardiac arrest includes the manifold.

* * * * *